United States Patent [19]

Wagner

[11] Patent Number: 4,483,987
[45] Date of Patent: Nov. 20, 1984

[54] 8-SUBSTITUTED 7-PHENYL-1,2,4-TRIAZOLO[2,3-C]PYRIMIDINES-5-AMINES AND AMIDES

[75] Inventor: Hans Wagner, Skokie, Ill.

[73] Assignee: G. D. Searle & Co., Skokie, Ill.

[21] Appl. No.: 506,157

[22] Filed: Jun. 20, 1983

[51] Int. Cl.³ ............................................. C07D 487/04
[52] U.S. Cl. ..................................................... 544/263
[58] Field of Search ........................................ 544/263

[56] References Cited

U.S. PATENT DOCUMENTS 3,046,276 7/1962 Miller et al. ......................... 544/263
3,053,844 9/1962 Miller et al. ......................... 544/263
4,405,780 9/1983 Wagner ................................ 544/263

Primary Examiner—Paul M. Coughlan, Jr.
Attorney, Agent, or Firm—Stuart L. Melton

[57] ABSTRACT

This invention relates to compounds having the formula

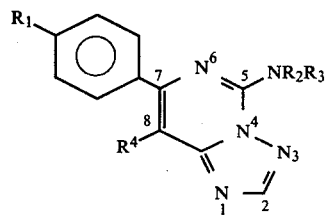

wherein $R_1$ represents hydrogen, halogen or alkoxy, $R_2$ and $R_3$ are hydrogen, alkanoyl or alkyl each being the same or different, $R_4$ represents alkanoyloxyalkyl, hydroxyalkyl, hydrogen, alkyl, alkoxyalkyl, alkenyl, alkynyl, adamantanecarbonyloxyalkyl, bromoalkyl or benzoyloxyalkyl.

28 Claims, No Drawings

8-SUBSTITUTED 7-PHENYL-1,2,4-TRIAZOLO[2,3-C]PYRIMIDINES-5-AMINES AND AMIDES

BACKGROUND OF THE INVENTION

This invention relates to 8-substituted 7-phenyl-1,2,4-triazolo[2,3-c]pyrimidine-5-amines and amides and the process for their preparation. More particularly, this invention provides new, useful and unobvious chemical compounds of formula I, useful as diuretics.

Diuretics are drugs used to increase the volume of urine excreted by the kidneys. They are employed principally for the relief of edema and ascites. These conditions occur in diseases of the heart, kidneys and liver. Diuretics are most effective in the treatment of cardiac edema, particularly that associated with congestive heart failure. They are also used in the ascites of cirrhosis, the nephrotic syndrome, diabetes insipidus, hypertension, edema of pregnancy, and to reduce cerebrospinal and intraocular fluid pressure. Some diuretics have highly specialized uses in glaucoma, hyperpotassemia, bromide intoxication, anginal syndrome, epilepsy, migraine, hypertension, and in premenstrual depression, conditions in which edema is not present or at least not definitely established.

The formation of urine from the blood, in simplest terms, consists of glomerular filtration and selective tubular reabsorption and secretion. As the glomerular filtrate passes through the tubules, substances essential to the blood and tissues—water, glucose, salts, and amino acids—are reabsorbed. Other substances in the glomerular filtrate, such as urea, are not as readily absorbed by the tubules. Thus, it is thought that in the renal tubule there is a specific mechanism for the transport of each ionic species, the capacities of which are quite different. For example, the capacity of the renal tubule to reabsorb sulfate ion is limited. The tubular capacity for the reabsorption of phosphate is such that sufficient is reabsorbed to maintain the normal extracellular level and any excess is excreted. On the other hand, much larger amounts of bicarbonate ion and chloride ion can be reabsorbed.

Thiazide diuretics act mainly to block sodium and chloride reabsorption at the first (thick) portion of the distal tubule. They also have a mild anti-carbonic anhydrase effect. The resulting natriuresis is accompanied by increased excretion of potassium, bicarbonate, chloride and water.

The antihypertensive action of the thiazides is attributable to two factors: (a) depletion of sodium and subsequent reduction in plasma volume and (2) a decrease in peripheral resistance. The latter is thought to be due either to the loss of sodium from the arteriolar wall or a direct action on the vascular bed. In addition, there is some inhibition of the pressor activity of norepinephrine. Quantitative hypersensitivity to diuretics is frequently encountered. Also possible is potassium deficiency pancreatitis, decreased glucose tolerance, increased uric acid levels and increased anticoagulent effect.

SUMMARY OF THE INVENTION

It has been found that novel compounds of the formula:

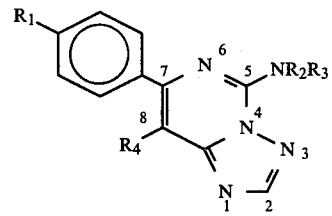

wherein
$R_1$ is:
(a) hydrogen;
(b) halogen; or
(c) alkoxy having from 1 to 6 carbon atoms, inclusive; with the proviso that $R_1$ is hydrogen only when $R_4$ is alkanoyloxyalkyl, hydroxyalkyl, adamantanecarbonyloxyalkyl, bromoalkyl or benzoyloxyalkyl;
wherein
$R_2$ or $R_3$ are:
(a) hydrogen;
(b) alkanoyl having from 1 to 6 carbon atoms, inclusive; or
(c) alkyl having from 1 to 6 carbon atoms, inclusive; $R_2$ and $R_3$ each being the same or different;
wherein
$R_4$ is:
(a) alkanoyloxyalkyl, the alkanoyl portion optionally being substituted by a carboxyl group on the terminal carbon and having from 1 to 10 carbon atoms, inclusive, and the alkyl portion having from 1 to 4 carbon atoms, inclusive;
(b) benzoyloxyalkyl, the alkyl portion having from 1 to 4 carbon atoms, inclusive, wherein the benzoyl group may optionally be substituted by 1 or 2 halo groups.
(c) adamantanecarbonyloxyalkyl, the alkyl portion having from 1 to 4 carbon atoms inclusive;
(d) hydroxyalkyl having from 1 to 4 carbon atoms inclusive;
(e) bromoalkyl having from 1 to 4 carbon atoms inclusive;
(f) hydrogen;
(g) alkyl having from 1 to 4 carbon atoms, inclusive;
(h) alkoxyalkyl having from 2 to 4 carbon atoms, inclusive;
(i) alkenyl having from 2 to 4 carbon atoms, inclusive;
(j) alkynyl having from 2 to 4 carbon atoms, inclusive; or
(k) alkylthioalkyl, each alkyl portion having from 1 to 4 carbon atoms, inclusive;
which are useful for their diuretic action similar to the thiazide diuretics but are a different chemical class.

Alkyl radicals and portions of radicals containing 1 to 10 carbon atoms include, for example, methyl, ethyl, propyl, butyl, pentyl, hexyl, heptyl, octyl, nonyl, decyl, and the isomeric forms thereof.

Those alkoxyalkyl radicals containing two to four carbon atoms and represented by $R_4$ include, for example, methoxymethyl, 1-methoxyethyl, 2-methoxyethyl, 2-methoxypropyl, 3-methoxypropyl, 1-ethoxyethyl, 2-ethoxyethyl, ethoxymethyl, propoxymethyl, and (1-methylethoxy)methyl and other isomeric forms thereof.

Those alkenyl and alkynyl radicals containing two to four carbon atoms include, for example, ethenyl, 1-propenyl, 2-propenyl, 1-butynyl, 2-butynyl, and 3-butynyl and other isomeric forms thereof.

The alkanoyl radicals or portions of radicals containing one to ten carbon atoms include, for example formyl, acetyl, propanoyl and other isomeric forms thereof.

Examples of halogen radicals include bromo and chloro.

Utility of a compound of the invention as a diuretic is established by statistical comparison of its dose response curve relative to that of hydrochlorothiazide with respect to urinary volume excretion. The laboratory protocol is derived from that of Lipshitz et al., J. Pharmacol. Exp. Ther. 79: 97-110, 1943, and the statistical methodology is based upon parallel line bioassay techniques discussed by Finney in Statistical Method in Biological Assay (2nd Edition) Charles Griffin & Company Limited, London, 1964.

Test animals are intact, normotensive male rats (Charles River Laboratories, Wilmington, Ma.) which are starved overnight with water ad lib. The animals are volume expanded on the day of the experiment with 25 ml/kg isotonic saline administered intragastrically. Experimental and standard compounds are administered as a suspension in the oral load. Hydrochlorothiazide is routinely used as the standard in this test at a dose of 0.2, 0.6 and 1.8 mg/kg. However, other standards may be used as deemed appropriate provided that potencies are clearly expressed in terms relative to that standard. Control animals are given isotonic saline alone.

Following saline and/or compound administration, rats are forced to void and are placed in pairs in clean, stainless steel metabolism cages for a 5 hour urine collection. At the end of 5 hours, rats are again forced to void residual bladder urine and are removed from the cage. Volume of urine is measured to the nearest 0.1 ml and expressed as a percentage of the initial saline load. Regression lines are compared statistically.

A compound is considered of superior potency if the 95% confidence limits of the calculated relative potency do not bracket unity. A compound is considered active if the diuretic response of the highest dose is significantly greater than a control response compared by analysis of variance at $P<0.05$.

By virtue of the above described activity the compounds of the invention are useful as diuretics and the compounds can be administered in a number of dosage forms. A preferred method of delivery would be orally. In any event, the compounds may be administered in any conventional manner. The compounds could be administered in oral unit dosage forms such as tablets, capsules, pills, powders or granules. They also may be administered rectally or vaginally in such forms as suppositories. They may be introduced in the forms of eyedrops, intraperitoneally, subcutaneously, or intramuscularly using forms known to the pharmaceutical art. Regardless of the route of administration selected, the compounds are formulated into pharmaceutically acceptable dosage forms by conventional methods known to the pharmaceutical art.

An effective but non-toxic quantity of the compound is employed for use as a diuretic. The dosage regimen for a diuretic by the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ relatively low dosages at first, subsequently increasing the dose until a maximum response is obtained.

The compounds of the invention may be made from compounds and methods described in U.S. Pat. No. 4,205,169 and U.S. patent application No. 06/352,913, now U.S. Pat. No. 4,405,780 which are both hereby incorporated by reference.

The invention will appear more fully from the Examples which follow. These Examples are given by way of illustration only and are not to be construed as limiting the invention either in spirit or in scope, as many modifications both in materials and methods will be apparent form the disclosure to those skilled in the art. Unless otherwise stated all temperatures are in degrees Celcius.

DESCRIPTION OF THE PREFERRED EMBODIMENTS

EXAMPLE 1

8-(2-hydroxyethyl)-7-phenyl-1,2,4-triazolo[2,3-c]pyrimidine-5-amine

To a solution of 28.8 g (0.1 mole) of 8-(2-ethoxyethyl)-7-phenyl-1,2,4-triazolo[2,3-c]pyrimidine-5-amine was added 200 ml of 1 N boron trichloride in dichloromethane. The mixture was then stirred at room temperature overnight, after which 500 ml of water was added. After three hours, the resultant precipitate was collected by filtration. The aqueous phase of the filtrate was separated and neutralized with aqueous sodium carbonate, giving a second precipitate. The combined solids were purified by column chromatography, giving the title compound, m.p. 194°-195°.

Analysis. Calcd. for $C_{13}H_{13}N_5O$: C, 61.17; H, 5.13; N, 27.43. Found: C, 60.75; H, 5.06; N, 27.40.

EXAMPLE 2

8-(2-acetyloxyethyl)-7-phenyl-1,2,4-triazolo[2,3-c]pyrimidine-5-amine

A solution of 25.5 g (0.1 mole) of the title compound of Example 1 and 11 ml (ca. 0.11 mole) of acetic anhydride in 150 ml of pyridine was allowed to stand for about 16 hours at room temperature. Approximately half of the solution was separated and concentrated in vacuo to dryness and chromatographed on silica gel, giving the title compound, m.p. 181°-182°.

Analysis. Calcd. for $C_{15}H_{15}N_5O_2$: C, 60.59; H, 5.08; N, 23.55. Found, C, 60.45; H, 5.08; N, 23.30.

EXAMPLE 3

N-[8-(2-acetyloxyethyl)-7-phenyl-1,2,4-triazolo[2,3-c]pyrimidin-5-yl]acetamide

To the remaining half of the solution described in Example 2 was added an additional 7 ml of acetic anhydride. After three days the mixture was concentrated in vacuo to dryness and then shaken with water and dichloromethane. The organic phase was washed with several portions of water, dried over sodium sulfate, filtered, and concentrated in vacuo to dryness. Purification by column chromatography afforded the title compound, m.p. 79°-80°.

Analysis Calcd. for $C_{17}H_{17}N_5O_3$: C, 60.16; H, 5.05; N, 20.64. Found: C, 60.55; H, 5.01; N, 20.86.

EXAMPLE 4

8-(2-octanoyloxyethyl)-7-phenyl-1,2,4-triazolo[2,3-c]pyrimidine-5-amine

The title compound, m.p. 89°–91°, was prepared by the method of Example 2 using 5.1 g (0.02 mole) of the product compound of Example 1 and 3.25 g (0.02 mole) of octanoyl chloride, except that the solution was not divided before purification.

Analysis Calcd. for $C_{21}H_{27}N_5O_2$: C, 66.11; H, 7.13; N, 18.36. Found: C, 65.57; H, 7.05; N, 18.29.

EXAMPLE 5

N-[8-(2-octanoyloxyethyl)-7-phenyl-1,2,4-triazolo[2,3-c]pyrimidin-5-yl]acetamide The title compound in Example 4 (3.2 g, 0.01 mole) was dissolved in 30 ml of pyridine to which was added 1.5 ml (ca. 0.015 mole) of acetic anhydride. After three days at room temperature, the mixture was concentrated in vacuo to dryness and purified by column chromatography on silica gel, giving the title compound, m.p. 69°–70°.

Analysis Calcd. for $C_{23}H_{29}N_5O_3$: C, 65.23; H, 6.90; N, 16.54. Found: C, 65.09; H, 6.86; N, 16.43.

EXAMPLE 6

8-(2-dimethylpropanoyloxyethyl)-7-phenyl-1,2,4-triazolo[2,3-c]pyrimidine-5-amine The title compound, m.p. 160°, was prepared by the method of Example 2 using 2.5 g (0.01 mole) of the product compound of Example 1 and 1.3 g (0.01 mole) of trimethylacetyl chloride, except that the reaction mixture was poured into 150 ml of water, giving a solid precipitate. Recrystallization from ethyl acetate/diethyl ether, rather than chromatography, afforded the title product.

Analysis Calcd. for $C_{18}H_{21}N_5O_2$: C, 63.70; H, 6.24; N, 20.63. Found: C, 63.54; H, 6.19; N, 20.82.

EXAMPLE 7

N-[8-(2-dimethylpropanoyloxyethyl)-7-phenyl-1,2,4-triazolo[2,3-c]pyrimidin-5-yl]acetamide The title compound is prepared by the method of Example 5 using 3.4 g (0.01 mole) of the product compound of Example 6.

EXAMPLE 8

8-(2-(2,4-dichlorobenzoyloxyethyl)-7-phenyl-1,2,4-triazolo[2,3-c]pyrimidine-5-amine The title compound, m.p. 181°–182°, was prepared by the method of Example 2 using 2.5 g (0.01 mole) of the product compound of Example 1 and 2.1 g (0.01 mole) of 2,4-dichlorobenzoyl chloride, except that the solution was not divided before purification.

Analysis Calcd. for $C_{20}H_{15}N_5O_2Cl_2$: C, 56.09; H, 3.53; N, 16.35; Cl, 16.56. Found: C, 56.46; H, 3.45; N, 15.96; Cl, 16.18.

EXAMPLE 9

N-[8-(2-(2,4-dichlorobenzoyloxyethyl)-7-phenyl-1,2,4-triazolo[2,3-c]pyrimidin-5-yl]acetamide The title compound is prepared by the method of Example 5 using the title compound of Example 8.

EXAMPLE 10

8-(2-(1-adamantanecarbonyloxy)ethyl)-7-phenyl-1,2,4-triazolo[2,3-c]pyrimidine-5-amine The title compound was prepared by the method of Example 2 using 2.5 g (0.01 mole) of the product compound of Example 1 and 2.0 g (0.01 mole) of 1-adamantanecarbonyl chloride, except that the solution was not divided before purification.

EXAMPLE 11

N-[8-(2-(1-adamantanecarbonyloxy)ethyl)-7-phenyl-1,2,4-triazolo[2,3-c]pyrimidin-5-yl]acetamide The title compound is prepared by the method of Example 5 using the title compound of Example 10.

EXAMPLE 12

8-(2-(3-carboxypropanoyloxy)ethyl)-7-phenyl-1,2,4-triazolo[2,3-c]pyrimidine-5-amine The title compound was prepared by the method of Example 2 using 2.5 g (0.01 mole) of the product compound of Example 1 and 1.0 g (0.01 mole) of succinic anhydride.

EXAMPLE 13

N-methyl-N-[8-(2-ethoxyethyl)-7-phenyl-1,2,4-triazolo[2,3-c]pyrimidin-5-yl]amine A mixture of 3.0 g (0.01 mole) of 8-(2-ethoxyethyl)-7-phenyl-1,2,4-triazolo[2,3-c]pyrimidine-5-amine, ca. 3 g of iodomethane, and ca. 1 g of potassium t-butoxide in t-butyl alcohol was stirred with heating for five hours. The solution was cooled to room temperature and then poured into 200 ml of cold water and extracted with several portions of ethyl acetate. The organic phase was washed with aqueous sodium chloride, dried over sodium sulfate, filtered, and concentrated in vacuo to dryness. Column chromatography on silica gel afforded 175 mg of the title monomethylated product.

Analysis Calcd. for $C_{16}H_{19}N_5O$: C, 64.63; H, 6.44; N, 23.55. Found: C, 64.19; H, 6.42; N, 23.11.

EXAMPLE 14

N-methyl-N-[8-(2-methoxyethyl)-7-phenyl-1,2,4-triazolo[2,3-c]pyrimidin-5-yl]amine A mixture of 3.0 g (0.008 mole) of the title product of Example 1, 3.3 g (0.023 mole) of iodomethane, and 1.75 g (0.016 mole) of potassium t-butoxide in 50 ml of t-butyl alcohol was stirred at room temperature for three hours. The mixture was poured into water and neutralized with acetic acid, then extracted with two portions of ethyl acetate. The organic extract was washed with brine, dried over sodium sulfate, filtered, and concentrated in vacuo. Column chromatography on silica gel afforded 77 mg of the N,O-dimethylated title compound, m.p. 133°–136°.

Analysis Calcd. for $C_{15}H_{17}N_5O$: C, 63.59; H, 6.05; N, 24.72. Found: C, 63.19; H, 6.04; N, 25.23.

EXAMPLE 15

N-methyl-N-[8-(2-hydroxyethyl)-7-phenyl-1,2,4-triazolo[2,3-c]pyrimidin-5-yl]amine Other chromatographic fractions from Example 14 afforded 101 mg of the N-methylated title compound, m.p. 160°–162°.

Analysis Calcd. for $C_{14}H_{15}N_5O$: C, 62.44; H, 5.61; N, 26.01. Found: C, 62.35; H, 5.56; N, 25.81.

EXAMPLE 16

8-(2-ethoxyethyl)-7-(4-methoxyphenyl)-1,2,4-triazolo[2,3-c]pyrimidine-5-amine The title compound, m.p. 176°–177°, was prepared from 4-chloro-5-(2-ethoxyethyl)-6-(4-methoxyphenyl)-pyrimidine-5-amine by methods described in U.S. patent application No. 06/352,913. That is, reaction with hydrazine hydrate afforded a crystalline hydrazine adduct. This adduct was allowed to react further with triethyl orthoformate in hot (140°–190°) triglyme to form a triazolo[4,3-c]pyrimidine intermediate which rearranged to the title compound. (The intermediate triazolo[4,3-c]pyrimidine, m.p. 221°–222.5°, was also isolated.) Structure assignment for the title compound was supported by the nmr spectrum and elemental analysis.

nmr (CDCl₃): (ppm) 8.45 (s, 1H, triazolo CH).

Analysis. Calcd. for $C_{16}H_{19}N_5O_2$: C, 61.33; H, 6.11; N, 22.35. Found: C, 61.22; H, 6.10; N, 22.01.

EXAMPLE 17

8-(2-ethoxyethyl)-7-(4-chlorophenyl)-1,2,4-triazolo[2,3-c]pyrimidine-5-amine The title compound, m.p. 183°–185°, was prepared from 4-chloro-5-(2-ethoxyethyl)-6-(4-chlorophenyl)-pyrimidine-5-amine by the method summarized in Example 16. (The corresponding triazolo[4,3-c]pyrimidine, m.p. 229°–231°, was also isolated.)

Analysis. Calcd. for $C_{15}H_{16}N_5OCl$: C, 56.70; H, 5.07; N, 22.04; Cl, 11.16. Found: C, 56.61; H, 4.86; N, 21.62; Cl, 11.53.

EXAMPLE 18

8-(2-hydroxyethyl)-7-(4-chlorophenyl)-1,2,4-triazolo[2,3-c]pyrimidine-5-amine The title compound, m.p. 207°–208°, was prepared by the method of Example 1 using the product compound of Example 17.

Analysis. Calcd. for $C_{13}H_{12}N_5OCl$: C, 53.89; H, 4.17; N, 24.17; Cl, 12.24. Found: C, 53.85; H, 4.12; N, 23.26; Cl, 12.75.

EXAMPLE 19

8-(2-bromoethyl)-7-phenyl-1,2,4-triazolo[2,3-c]pyrimidine-5-amine

To 2.8 g of 8-(2-ethoxylethyl)-7-phenyl-1,2,4-triazolo[2,3-c]pyrimidine-5-amine dissolved in 30 ml of chloroform was added 5 ml of boron tribromide (1 M solution in dichloromethane) at room temperature with stirring. After 8 hours the complex was decomposed by the addition of ice water. The phases were separated and the aqueous layer was adjusted to pH 8 with potassium carbonate, then extracted three times with chloroform. The chloroform extract was added to the original chloroform layer, and the resultant solution was washed with water and dried over sodium sulfate. Removal of chloroform followed by chromatography on Porosil afforded, in order of elution, title compound (m.p. 163°–164°), and title compound Example 1, (m.p. 193°–194°)

EXAMPLE 20

8-(2-ethylthioethyl)-7-phenyl-1,2,4-triazolo[2,3-c]pyrimidine-5-amine

To a solution of 1.08 g (9.7 mmole) of potassium t-butoxide in 30 ml of cold (circa 0°) t-butyl alcohol was added 0.8 g (12.9 mmole) of mercaptoethanol, and the mixture was allowed to warm to room temperature. The title compound of Example 19 (2.05 g, 6.4 mmole) was added and the mixture was heated at reflux for two hours. Upon cooling, the mixture was concentrated in vacuo and the residue was treated with 50 ml of water. The mixture was extracted with chloroform/dichloromethane and the organic phase was washed with water, dried over magnesium sulfate, filtered, and concentrated to dryness. Column chromatography of the crude product on silica gel afforded 350 mg of the title compound, m.p. 120°–122°.

Analysis. Calcd. for $C_{15}H_{17}N_5S$: C, 60.18; H, 5.72; N, 23.39; S, 10.71. Found: C, 60.22; H, 5.80; N, 23.21; S, 10.63.

What is claimed is:

1. A compound of the formula

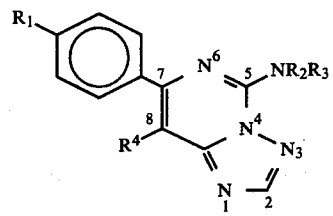

wherein
$R_1$ is:
(a) hydrogen;
(b) halogen; or
(c) alkoxy having from 1 to 6 carbon atoms, inclusive, with the proviso that $R_1$ is hydrogen only when $R_4$ is alkanoyloxyalkyl, benzoyloxyalkyl, adamantanecarbonyloxyalkyl, hydroxyalkyl or bromoalkyl;

wherein
$R_2$ or $R_3$ are:
(a) hydrogen;
(b) alkanoyl having from 1 to 6 carbon atoms inclusive; or
(c) alkyl having from 1 to 6 carbon atoms, inclusive; $R_2$ and $R_3$ each being the same or different;

wherein
$R_4$ is:
(a) alkanoyloxyalkyl, the alkanoyl portion optionally being substituted by a carboxyl group on the terminal carbon and having from 1 to 10 carbon atoms, inclusive and the alkyl portion having from 1 to 4 carbon atoms inclusive;
(b) benzoyloxyalkyl, the alkyl group having from 1 to 4 carbon atoms, inclusive, wherein the benzoyl group may optionally be substituted by 1 or 2 halo groups,
(c) adamantanecarbonyloxyalkyl, the alkyl portion having from 1 to 4 carbon atoms, inclusive;
(d) hydroxyalkyl having from 1 to 4 carbon atoms, inclusive;
(e) bromoalkyl having from 1 to 4 carbon atoms, inclusive;

(f) hydrogen;
(g) alkyl having from 1 to 4 carbon atoms, inclusive;
(h) alkoxyalkyl having from 2 to 4 carbon atoms, inclusive;
(i) alkenyl having from 2 to 4 carbon atoms, inclusive; or
(j) alkynyl having from 2 to 4 carbon atoms, inclusive; or
(k) alkylthioalkyl the alkyl portions each having from 1 to 4 carbon atoms, inclusive.

2. A compound according to claim 1 wherein $R_4$ is hydroxyalkyl.

3. 8-(2-hydroxyethyl)-7-phenyl-1,2,4-triazolo[2,3-c]pyrimidine-5-amine, a compound according to claim 2.

4. N-methyl-N-[8-(2-hydroxyethyl)-7-phenyl-1,2,4-triazolo[2,3-c)pyrimidin-5-yl]amine, a compound according to claim 2.

5. 8-(2-hydroxyethyl)-7-(4-chlorophenyl)-1,2,4-triazolo[2,3-c]pyrimidine-5-amine, a compound according to claim 2.

6. A compound according to claim 1 wherein $R_4$ is alkanoyloxyalkyl, the alkanoyl portion optionally substituted by a carboxyl group on the terminal carbon.

7. 8-(2-acetyloxyethyl)-7-phenyl-1,2,4-triazolo[2,3-c]pyrimidine-5-amine, a compound according to claim 6.

8. N-[8-(2-acetyloxyethyl)-7-phenyl-1,2,4-triazolo[2,3-c]pyrimidin-5-yl]acetamide, a compound according to claim 6.

9. 8-(2-octanoyloxyethyl)-7-phenyl-1,2,4-triazolo[2,3-c]pyrimidine-5-amine, a compound according to claim 6.

10. N-[8-(2-octanoyloxyethyl)-7-phenyl-1,2,4-triazolo[2,3-c]pyrimidin-5-yl]acetamide, a compound according to claim 1.

11. 8-(2-(2,2-dimethylpropanoyloxy)ethyl)-7-phenyl-1,2,4-triazolo[2,3-c]pyrimidine-5-amine, a compound according to claim 6.

12. N-[8-(2-(2,2-dimethylpropanoyloxy)ethyl)-7-phenyl-1,2,4-triazolo[2,3-c]pyrimidin-5-yl]acetamide, a compound according to claim 6.

13. 8-(2-(3-carboxypropanoyloxy)ethyl)-7-phenyl-1,2,4-triazolo[2,3-c]pyrimidine-5-amine, a compound according to claim 6.

14. A compound according to claim 1 wherein $R_4$ is benzoyloxyalkyl the alkyl group having from 1 to 4 carbon atoms, inclusive, wherein the benzoyl group may optionally be substituted by 1 or 2 halo groups.

15. 8-(2-(2,4-dichlorobenzoyloxy)ethyl)-7-phenyl-1,2,4-triazolo[2,3-c]pyrimidine-5-amine]acetamide, a compound according to claim 14.

16. N-[8-(2-(2,4-dichlorobenzoyloxy)ethyl)-7-phenyl-1,2,4-triazolo[2,3-c]pyrimidin-5-yl]acetamide, a compound according to claim 14.

17. A compound according to claim 1 wherein $R_4$ is adamantanecarbonyloxyalkyl, the alkyl portion having from 1 to 4 carbon atoms, inclusive.

18. 8-(2-(1-adamantanecarbonyloxy)ethyl)-7-phenyl-1,2,4-triazolo[2,3-c]pyrimidine-5-amine, a compound according to claim 17.

19. N-[8-(2-(1-adamantanecarbonyloxy)ethyl)-7-phenyl-1,2,4-triazolo[2,3-c]pyrimidin-5-yl]acetamide, a compound according to claim 17.

20. A compound according to claim 1 wherein $R_4$ is alkoxyalkyl having from 1 to 4 carbon atoms, inclusive.

21. N-methyl-N-[8-(2-ethoxyethyl)-7-phenyl-1,2,4-triazolo[2,3-c]pyrimidin-5-yl]amine, a compound according to claim 20.

22. N-methyl-N-[8-(2-methoxyethyl)-7-phenyl-1,2,4-triazolo[2,3-c]pyrimidin-5-yl]amine, a compound according to claim 20.

23. 8-(2-ethoxyethyl)-7-(4-methoxyphenyl)-1,2,4-triazolo[2,3-c]pyrimidine-5-amine, a compound according to claim 20.

24. 8-(2-ethoxyethyl)-7-(4-chlorophenyl)-1,2,4-triazolo[2,3-c]pyrimidine-5-amine, a compound according to claim 20.

25. A compound according to claim 1 wherein $R_4$ is bromoalkyl, the alkyl portion having from 1 to 4 carbon atoms, inclusive.

26. 8-(2-bromoethyl)-7-phenyl-1,2,4-triazolo[2,3-c]pyrimidine-5-amine, a compound according to claim 25.

27. A compound according to claim 1 wherein $R_4$ is alkylthioalkyl, each alkyl portion having from 1 to 4 carbon atoms inclusive.

28. 8-(2-ethylthioethyl)-7-phenyl-1,2,4-triazolo[2,3-c]-pyrimidine-5-amine, a compound according to claim 27.

* * * * *